(12) United States Patent
Bridger et al.

(10) Patent No.: US 6,887,199 B2
(45) Date of Patent: May 3, 2005

(54) BRAIN ASSESSMENT MONITOR

(75) Inventors: Keith Bridger, Washington, DC (US); Arthur V. Cooke, Baltimore, MD (US); Philip M. Kuhn, Severna Park, MD (US); Joseph J. Lutian, Arnold, MD (US); Edward J. Passaro, Towson, MD (US); John M. Sewell, Cockeysville, MD (US); Terence V. Waskey, Centerville, MD (US); Gregg R. Rubin, Baltimore, MD (US)

(73) Assignee: Active Signal Technologies, Inc., Linthicum, MD (US)

( * ) Notice: Subject to any disclaimer, the term of this patent is extended or adjusted under 35 U.S.C. 154(b) by 294 days.

(21) Appl. No.: 10/095,861

(22) Filed: Mar. 12, 2002

(65) Prior Publication Data

US 2002/0198469 A1 Dec. 26, 2002

Related U.S. Application Data

(63) Continuation-in-part of application No. 09/401,762, filed on Sep. 23, 1999, now Pat. No. 6,491,647.
(60) Provisional application No. 60/275,046, filed on Mar. 12, 2001.

(51) Int. Cl.$^7$ .............................................. A61B 5/00
(52) U.S. Cl. ..................... 600/300; 128/920; 600/544
(58) Field of Search ................................. 600/300–301, 600/544–545, 500, 587, 503, 437, 586, 561, 485; 128/920, 898

(56) References Cited

U.S. PATENT DOCUMENTS

| | | | |
|---|---|---|---|
| 5,388,583 A | 2/1995 | Ragauskas et al. | |
| 5,617,873 A | 4/1997 | Yost et al. | |
| 5,951,476 A | * 9/1999 | Beach | ........................ 600/437 |
| 6,231,516 B1 | 5/2001 | Keilman et al. | |
| 6,328,694 B1 | 12/2001 | Michaeli | |

* cited by examiner

Primary Examiner—Max F. Hindenburg
Assistant Examiner—Michael Astorino
(74) Attorney, Agent, or Firm—Alan G. Towner, Esq.; Lara A. Northrop, Esq.; Pietragallo, Bosick & Gordon

(57) ABSTRACT

A non-invasive brain assessment monitor is disclosed. An embodiment of the monitor includes a head-mounted brain sensor which passively senses acoustic signals generated from pulsing blood flow through a patient's brain. A reference sensor may be mounted at another location on the patient's body to sense an arterial pulse, and the signals from the brain sensor and reference sensor may be compared. Another embodiment includes transmitters which generate acoustic signals in the brain which are also detected by the brain sensor. The brain assessment monitor may be used to detect conditions such as head trauma, stroke and hemorrhage.

43 Claims, 7 Drawing Sheets

BRAIN ASSESSMENT MONITOR

CROSS REFERENCE TO RELATED APPLICATIONS

This application claims the benefit of U.S. Provisional Application Ser. No. 60/275,046 filed Mar. 12, 2001. This application is a continuation-in-part of U.S. application Ser. No. 09/401,762 filed Sep. 23, 1999, now U.S. Pat. No. 6,491,647.

GOVERNMENT CONTRACTS

The United States Government has certain rights to this invention pursuant to Contract Nos. 1 R43 NS-41843-01 and 2 R44 NS-38825-02 awarded by the National Institutes of Health.

FIELD OF THE INVENTION

The present invention relates to brain assessment monitors, and more particularly relates to monitors which detect brain trauma, stroke, tumors and changes in blood flow patterns through the brain as a result of injury or disease.

BACKGROUND INFORMATION

In a healthy human, the integrity of the physiology is such that signals emanating from the heart are well coupled to other parts of the anatomy through the arterial system. Examples are radial pulse signals and heart sounds picked up at the chest.

Existing clinical systems that are used to assess anomalies such as brain trauma, stroke and tumors include computed tomography (CT) scans, magnetic resonance imaging (MRI) and, in the case of brain trauma monitoring, combinations of these with invasive intra ventricular catheters (IVC) or subarachnoid bolts to directly measure intracranial pressure (ICP). There is, however, currently, no way to determine brain disorder without such equipment, leaving decisions on treatment to be delayed in the case of stroke until it can be determined whether the stroke is a bleed or ischemia. In a similar fashion, persons injured at the scene of an accident must be presumed to be brain injured, even if the cause of their non-responsiveness arises from the effects of drugs or alcohol. Another large category of head injuries are those resulting from falls, particularly in the elderly. Immediate assessment of injury would be most helpful while awaiting more comprehensive diagnosis. Non-invasive assessment systems do not exist to determine physiological changes in the brain as a result of injury or disease. This prevents early intervention in the critical time after the brain is first damaged.

Approximately three-quarters of a million individuals suffer from stroke each year in the United States. More than 80 percent of these strokes are caused by occlusion of an artery supplying blood to brain cells (ischemic), the type which might be amenable to therapy with the clot busting medicine, tissue plasminogen activator (TPA). TPA has been shown to significantly reduce disability, but this medication must be given within a short time, typically 3 hours, after stroke symptoms begin. This time window, which tracks damage that begins within minutes after the onset of stroke, is similar to that for trauma patients, and it is known as the "golden window". TPA treatment is, however, not without risk, because its clot dispersion action raises the potential for intracranial hemorrhage. Due to this side effect it cannot be given to patients who have a stroke caused by bleeding into the brain, termed a hemorrhagic stroke. At the present time, medical treatment awaits the brain CT scan and clinical diagnosis from a skilled team to determine the type of stroke, very often precluding intervention during the precious initial three to six hours. The current system will allow a medic on the scene to differentiate brain ischemia from brain hemorrhage and should significantly increase the percentage of stroke patients who would benefit from TPA and other time-sensitive therapies.

Nearly 2 million people suffer some type of traumatic brain injury each year resulting in 50,000 deaths and high costs to the healthcare system. In order to receive optimum treatment for brain injury, the injury must be diagnosed and treatment begun within one hour after the initial injury. The difficulty is that approximately 50 percent of brain related injuries are drug or alcohol related, generating confusion in the distinction between a person's unresponsiveness as arising from traumatic brain injury (TBI) as distinct from the effects of alcohol or drugs. This lack of diagnostic capability results in the transportation of non-injured patients to trauma centers as well as detracting from the time and effort devoted to the truly injured.

In both stroke and trauma, the current diagnostic capability resides in emergency rooms or trauma centers where there have been tremendous technical advances in brain imaging (MRI and CT scans), flow analysis in cervicocranial arteries, including subtraction angiography, magnetic resonance angiography (MRA), computed tomography angiography (CTA), and extracranial and transcranial Doppler. To date, only the brain CT scan and, in special circumstances, a brain MRI scan can detect changes in brain tissue that indicate either brain ischemia or brain hemorrhage in the case of stroke or various other disturbances to the parenchyma in the case of traumatic brain injury (TBI). Both of these are considered to some extent invasive or intrusive. The use of the non-invasive diagnostic aids, such as continuous wave and pulsed Doppler (Duplex) as well as transcranial Doppler (TCD) have grown as well. Sometimes, a combination of magnetic resonance angiography (MRA) and ultrasound can be useful diagnostic tools for stroke in the hands of a specialist. However, often the accuracy of some of these non-invasive techniques, such as TCD, are technician dependent and these tools are not available to the emergency medical services (EMS) personnel at the scene where transport decisions must be made.

An intracranial pressure (ICP) monitor is disclosed in U.S. Pat. No. 5,919,144, which is incorporated herein by reference. The ICP monitor, which may be used for patients with traumatic brain injury, provides active ensonification of the brain with a known frequency and amplitude of input signal. The change in this signal after transmission through the brain is picked up at a receiving sensor disposed on the outside of the head and the measured change is used to assess brain tissue disturbance.

SUMMARY OF THE INVENTION

A principal use of the present brain assessment monitor is detecting injury to the brain caused by stroke or trauma. Although trauma generally causes brain damage globally throughout the mass of the parenchyma and stroke causes damage that is focal, both alter the acoustic transmission properties of the brain enabling detection in accordance with the present invention. Arterial conducted heart pulses are coupled to the brain so that the brain pulses in phase with the heart when the time lag for signal propagation is taken into account. However, when the brain is disturbed through injury or disease, the consistency of the brain changes such that the signal that is sensed at the skull using a sensitive detecting device is no longer a replica of the arterial pulse wave. This signal anomaly arises from phenomena such as lack of perfusion in the brain, edema causing decreased compliance and consequent loss of perfusion, and infarcts which alter the consistency of the brain tissue and hence its acoustic properties. This latter effect accompanies brain tumors as well. Beyond brain injury or disease, signal anomalies can also be seen in intra-operative loss of perfusion in the brain where circulation can be impaired for periods of time during procedures such as open-heart surgery. The same principles apply when measuring alterations of flow patterns in the circulatory system arising from impediments to flow, such as clots that may occur downstream from the heart, and can be detected at an artery beyond the clot.

An embodiment of the present invention provides a low-power acoustic approach for brain damage assessment in a compact, portable package that can be readily transported to and applied at the scene of stroke or brain injury. A small, portable device is used to directly measure brain disturbance and blood flow characteristics in the brain. Brain tissue has very different acoustic transmission characteristics from normal tissue. This effect is measurable with a passive contact sensor mounted on a patient's head.

An embodiment of the present invention relates to a simple, portable, small brain assessment tool suitable for rapid measurement in situations of potential brain impairment, including trauma, hematoma, stroke, tumors and the like. It comprises a superficially applied sensor, signal conditioning electronics, data capture hardware and software, means for signal processing and interpretation and display means. A sensor or sensors are applied to any one of a number of locations on a person's head and the signal emanating from the brain is recorded for analysis of the waveform characteristics. The system may also include another reference sensor on a representative artery elsewhere in the body that more closely reflects the waveform characteristics of the heart and thus acts as the reference signal for the brain sensor. The system may optionally further include active generation of an independent signal at some point of the brain away from the receiver, and detection of the signal quality of the received signal as a function of the input signal. The signals may then be analyzed through time domain observation for a first approximation and then through signal processing techniques to obtain more precise information on the nature of the disturbance.

An aspect of the present invention is to provide a non-invasive brain assessment monitor comprising a brain sensor for sensing acoustic signals generated from pulsing blood flow through a patient's brain, and means for analyzing the acoustic signals in order to determine whether the patient has undergone a brain injury and/or disease.

Another aspect of the present invention is to provide a non-invasive brain assessment monitor comprising a brain sensor configured and adapted for mounting on a patient's head, a reference sensor configured and adapted for mounting at another location on the patient's body, and means for comparing signals from the brain sensor and the reference sensor to determine whether the patient has undergone a brain injury and/or disease.

A further aspect of the present invention is to provide a method of monitoring brain injury and/or disease of a patient comprising mounting a brain sensor on the head of the patient, sensing acoustic signals with the brain sensor generated from pulsing blood flow through the patient's brain, and analyzing the acoustic signals to determine whether the patient has undergone a brain injury and/or disease.

Another aspect of the present invention is to provide a method of monitoring brain injury and/or disease of a patient comprising mounting a brain sensor on the patient's head, mounting a reference sensor at another location on the patient's body, and comparing signals from the brain sensor and the reference sensor to determine whether the patient has undergone a brain injury and/or disease.

These and other aspects of the present invention will be more apparent from the following description.

BRIEF DESCRIPTION OF THE DRAWINGS

FIG. 3 also illustrates optional transducers mounted on a patient's head in order to provide active brain assessment monitoring in accordance with another embodiment of the present invention.

DETAILED DESCRIPTION

Figure 1:
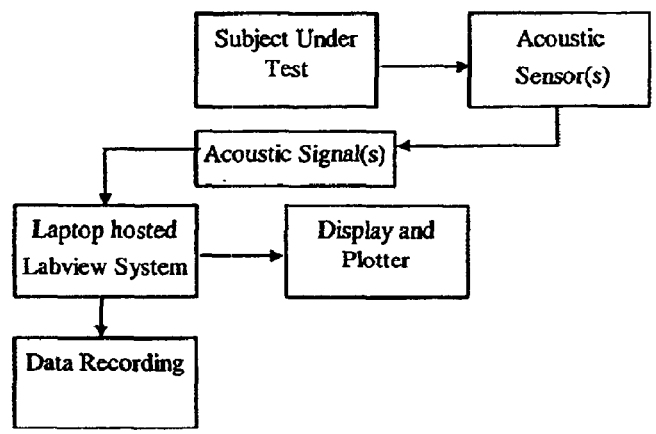
FIG. 1 is a schematic diagram illustrating a passive brain assessment monitor system in accordance with an embodiment of the present invention.

As shown in FIG. 1, the brain assessment monitor according to the present invention comprises an acoustic sensor, which may be mounted on a patient's head. In addition to the brain sensor, another reference sensor may be mounted at another location on the patient's body, for example, on an artery such as the carotid or radial in order to provide a comparison signal. The sensor output(s) may be fed to an acoustic signal conditioning system for purposes of filtering, amplification and noise elimination. The conditioned signals may be analyzed through the use of a suitable signal analyzer to determine their time and frequency domain characteristics.

Figure 2:
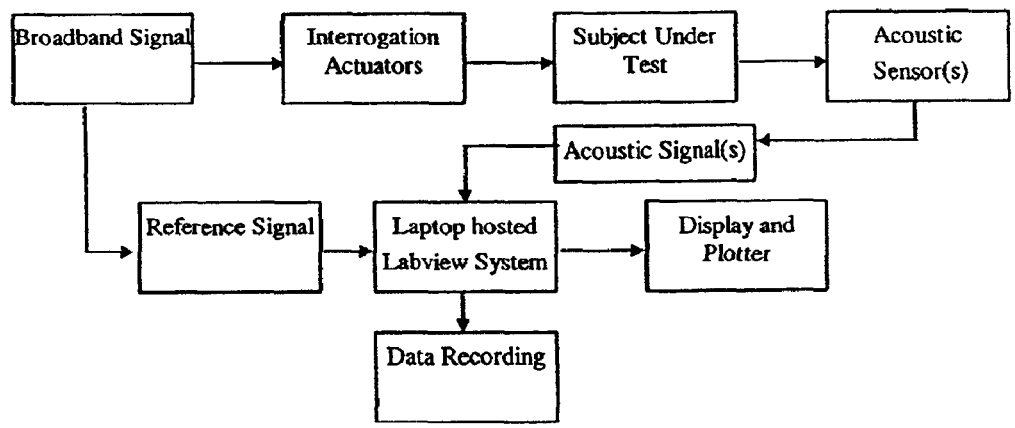
FIG. 2 is a schematic diagram illustrating an active brain assessment monitor system in accordance with an embodiment of the present invention.

In one embodiment of the invention, as illustrated in FIG. 2, an active component may be added to the system comprising acoustic signal transmitters or actuators applied to one or more positions on the head. The input signal to the actuators may be a sinusoidal tone that is swept in frequency across the range of interest (generally 10–1000 Hz) or may be broadband noise, in which case several pulses of the noise and averaging techniques may have to be used. The transmitted signal may also be fed as a reference signal to the signal analyzer.

Figure 3:
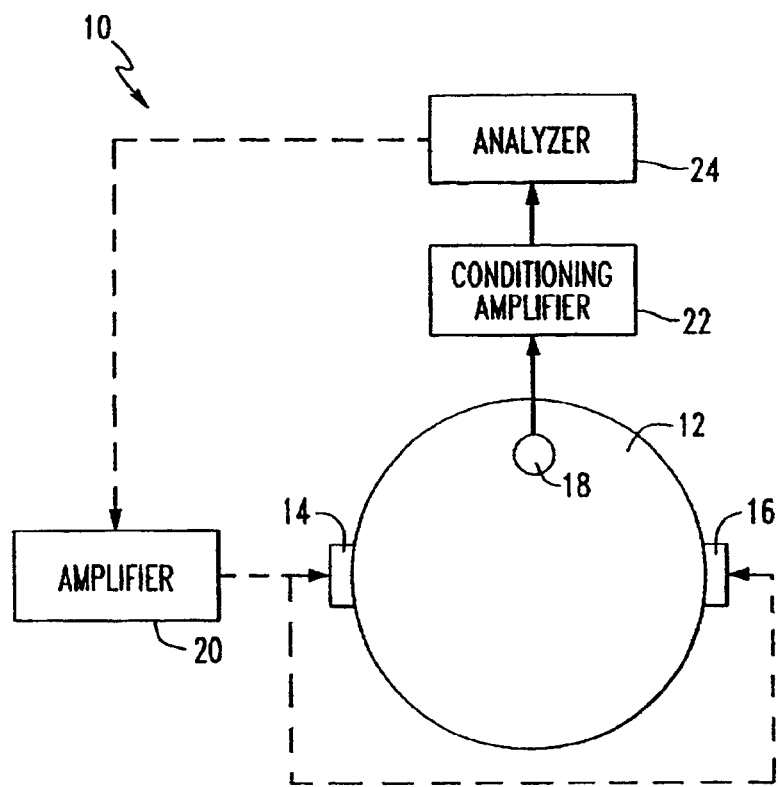
FIG. 3 is a partially schematic illustration of a brain assessment monitor positioned on a patient's head in accordance with an embodiment of the invention.

FIG. 3 schematically illustrates a brain assessment monitor 10 in accordance with an embodiment of the present invention. An acoustic brain sensor 18 is mounted on a patient's head 12. Acoustic signals detected by the brain sensor 18 are transmitted to a conditioning amplifier 22, then to an analyzer 24.

The brain sensor 18 is preferably a sensor which is matched to the acoustic properties of the brain such that it can discriminate changes in amplitude of sound transmission, e.g., as fine as 0.1 dB at frequencies from 0.5 Hz to 2,000 Hz. The brain sensor 18 may be of any suitable type such as piezoelectric, micro electromechanical, piezoelectric polymer, magnetic film, magnetostrictive, strain gauge, fiber optic, moving coil type and geophone sensors, with piezoelectric sensors being preferred for many applications. Devices such as air coupled electronic stethoscopes may also be effective. Particularly suitable brain sensors comprise active sensing elements such as piezoelectric ceramics incorporated into mechanical designs that amplify the magnitude of the received displacement at the expense of some force. An example is the Morgan Matroc Adrenal Pressure Sensor which consists of a piezoelectric bimorph, comprising two extremely thin piezoelectric plates mounted on either side of a fine brass vane, in the form of a narrow ribbon mounted in a metal housing with lever mechanisms to increase the displacement amplitude received at the bimorph.

The brain sensor 18 of the present invention is preferably placed in contact with the head at any suitable location which allows sensing of acoustic signals from the parenchyma. In a preferred embodiment, a single brain sensor is centrally located on a subject high on the forehead above the sinus cavities. The acoustic brain sensor 18 is ideally placed directly on the skin with no gels or pads. Although the brain sensor 18 may be placed at some point on the surface of the skull over the brain area, such as on the forehead above the area covering the sinus cavity, it may also be placed at the top of the head where the response has been found to be often more sensitive. The brain sensor 18 may be held in place with a band so that there is no interference in the signal from a hand holding the sensor. To allow the brain sensor 18 to seat and couple well to the person's skull through flesh and skin, a short period of time may be required.

The signal from the brain sensor 18 may be conditioned and amplified by the conditioning amplifier 22, such as a B&K Model 2635 amplifier. The conditioning amplifier 22 may adjust the apparent impedance of the brain sensor 18 so that it can be read by the analyzer 24, and may also increase signal-to-noise ratio by filtering spurious signals. The signal is then acquired by the analyzer 24 for analysis according to power, frequency, impedance, etc. The analyzer 24 may display and/or record a trace corresponding to the acoustic signal received by the brain sensor 18.

In accordance with an embodiment of the invention, a patient may be monitored in an active mode by mounting acoustic signal transmitters 14 and 16 at the temples of the subject, or any other suitable location, as shown by the dashed lines in FIG. 3. The optional transmitters 14 and 16 for the active system may be, for example, small hearing aid speakers, which are reconfigured to couple directly to the side of the head. One transmitter may be positioned at each side of the head in the temporal area. The transmitters 14 and 16 can be held under the same elasticized band as the brain sensor(s), e.g., with the transmitters at the temples and the brain sensor at the forehead.

The frequency capability of the transmitters 14 and 16 may be, for example, from 20 Hz to 15,000 Hz. A low voltage acoustic instrument amplifier may be used, and the pair of transmitters may generate low milliwatts of power, far below known safety levels of acoustic energy, impinging upon the brain but adequate to ensonify the brain with a signal readily detectable by the receivers. A power amplifier 20 such as a B&K Model 2706 amplifier provides electronic signals to the acoustic signal transmitters 14 and 16. The signal analyzer 24, such as a Hewlett-Packard HP3562A, may be used to generate a signal to the power amplifier 20 which drives the acoustic signal transmitters 14 and 16.

In the active mode, the brain is ensonified with the transmitters 14 and 16, and the resulting signal after interaction with the brain is picked up by the brain sensor 18. The analyzer 24 may include a signal processing system having fast fourier transform (FFT), peak amplitude detection, and integrated energy calculation capabilities. The frequency content or spectrum of the signal obtained by FFT may be used to characterize the acoustic response of the brain. The fourier transform is preferably carried out in close to real-time, such that the frequency content of a signal, averaged over very short time sequences, can be seen as it is being received. The analyzer 24 may be integrated with the power amplifier 20 and can be used to compare the acoustic signals generated by the power amplifier 20 with the acoustic signals received by the receiver 18.

In both the passive and active modes, the acquisition may be part of a Labview system used on a laptop computer. This system acts as a signal analyzer, and may act as a signal source in active embodiments. In one embodiment, the necessary signal processing is conducted on a laptop computer with a PCMCIA card that serves both as the signal generator and data acquisition system, and may also serve as a signal generator. The analyzer permits various types of signal analysis including frequency response measurements, time domain signal analysis, and power spectrum measurements. The measurements for the latter type of signals are those of very low frequency, i.e., brain pulsatile energy as emanating from intracranial arteries. A frequency response may be measured in an active interrogation mode by dividing the signal at the sensor by the input signal (a subtraction when the signal levels are expressed in dB).

Figure 4:
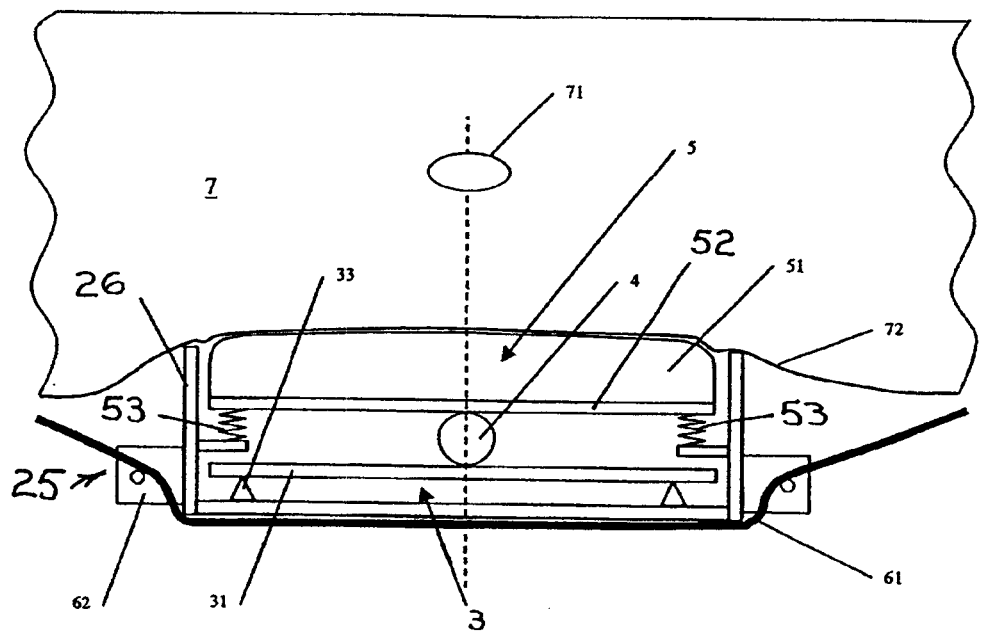
FIG. 4 is a partially schematic side view of a reference sensor mounted adjacent to a patient's artery in accordance with an embodiment of the present invention.

FIG. 4 illustrates an embodiment of a reference sensor 25 which may be used to detect an arterial pulse signal in accordance with an embodiment of the present invention. The reference sensor 25 includes a sensing element 31 contained in a rigid or semi-rigid housing 26. The housing 26 may comprise a protective mounting enclosure made of plastic, composite, rubber, metal or other suitable material with a base and sidewalls to form an opening at one end. An interface transition mechanism 5 is defined by an outer contact member 51, a stiffening member 52, and compliant return elements 53. The stiffening member 52, such as a thin metallic sheet, ensures that all forces and displacements incident on outward facing surface of the outer contact member 51 are transmitted efficiently to a load transfer element 4. The compliant return elements 53, such as springs or elastomeric pads maintain initial orientation and position of the outer contact member 51 relative to the housing 26. Accordingly, the outer contact member 51 is very loosely mounted, or essentially free floating.

As shown in FIG. 4, the interface transition mechanism 5 of the reference sensor 25 contacts the load transfer element 4, such as a hard spherical contacter, which in turn contacts a sensing portion 3. The sensing portion 3 may comprise a suitable sensor, such as piezoelectric bimorph 31 mounted on support members 33. The components are mechanically arranged to enable forces incident at almost any angle on outer surface of the outer contact member 51 to be transmitted effectively to the most sensitive region of the sensing portion 3. A signal is measured when the load transfer element 4 transmits forces to the sensing portion 3.

As shown in FIG. 4, the reference sensor is mounted against an outer surface 72 of a human or animal body 7 and held in place with a strap 61 and tabs 62. Tension of the strap 61 is adjusted to provide a comfortable wearing pressure of the device 1 against the body 7 and ensure intimate interfacial contact. The outer contact member 51 is centered approximately over the area of the body surface 72 where the displacement or force deriving from a physiological source 71 such as an arterial pulse is manifest. The displacement or force is effectively transmitted via the outer contact member 51, stiffening member 52 and load transfer element 4 onto the sensing elements 31. The pulse signals detected by the reference sensor 25 may be compared with the signals detected by the brain sensor 18 in order to detect brain trauma, stroke, etc.

The displayed signal emanating from the brain of a healthy person resembles an arterial pulse wave as sensed at any other major artery in the body. While there is a visual similarity, it is important to distinguish the current sensing modality from conventional arterial waveform recording as conducted using a pressure transducer in-situ in the artery. Sensor types like piezoelectrics used in the present invention have largely capacitive electrical characteristics. As a consequence, the signal corresponding to a positive oscillating pressure signal has both positive and negative components. The capacitive feature means that the total area under the positive and negative going curves is equal, but the height of the positive and negative peaks will vary depending on the brain condition of the patient. In a person with a normal healthy brain, the ratio of positive to negative peak heights will be a minimum of about 2:1. In a person with a brain injury, this signal is both distorted from an ideal arterial pulse wave form and most frequently the ratio of positive to negative going peaks is reduced.

Although stroke and trauma patients do not have the same pathologies, both conditions are manifest in altered brain consistency or integrity and thus produce signal traits that distinguish them from normal subjects. Stroke traits may be different from those observed with trauma. Further, stroke patients will have signal characteristics that distinguish ischemia from hemorrhage.

The observed change in signal characteristics from normal to pathological brain states has to do with changes in acoustic properties as a result of injury. The physiological cause of the signal change parallels the causes of alteration in cerebral perfusion. The signal change reflects the condition of the brain that may be causing increases in ICP and reduction in cerebral perfusion pressure (CPP). This feature is important because patients with severe head injury can often have controlled ICP but remain in poor neurological state or even worsen. In the period immediately after TBI the brain will experience a sharp drop in cerebral blood flow (CBF) and correspondingly, the signal will also decrease in amplitude, ratio and become distorted. Where the ICP increases and the autoregulation system is impaired causing a reduction in cerebral perfusion pressure, the signal will be similarly degraded. While cerebral perfusion is only one phenomenon that matches the signal alteration, it is associated with others that are related to the same flow effects, i.e., loss of compliance in the brain, constriction of arteries, especially arterioles, etc. In addition to flow properties of the brain, there appear to be impedance changes in the brain. While these are related, the mechanism for change in the latter may be associated with changes in the characteristics of the venules which transition cerebral blood flow from the major arteries to the fine capillary structure of the vascular bed. With increasing ICP, edema and other physical changes in consistency of parenchyma, the venules become collapsed to some extent—they hold less blood and thus the acoustic properties of the brain change.

Following signal capture, several variables can be separated by standard signal processing techniques that generate a more refined picture of the presence or nature of an injury. For example, when a fast Fourier transform (FFT) is performed on a time domain signal of a healthy person, the harmonic content beginning with the first or second harmonic and often with the fundamental, begins a monotonic descent in energy level until. Around 30 Hz it has decayed by approximately −40 dB below the maximum energy level observable in the FFT. In an injured person, this FFT often displays a fundamental that is not the repetition rate of the heart (typically close to 1 Hz) but a higher tone, caused by the distorted signal. Also, the energy in spectral peaks above 5 Hz will often rise before beginning to fall again at the higher frequencies. Consequently, the energy in the spectrum of head-injured patients is often greater in higher frequency bands than that of healthy subjects.

In addition, there are other components of the signal arising from known sources such as the ICP signal itself, vaso spasms, flow interruptions, or even unknown sources that generate components of the signal that are not replicas in any form of the arterial pulse. These can be separated by signal processing through the use of reduction of discrete components of the signal, sometimes after beginning with an arterial pulse sensed, for example, at the radial artery, subtracted from the scaled waveform sensed at the head to eliminate individual variables and focus on disturbances of the signal caused by the pathology itself.

As used herein, the term "attenuation" means a reduction in amplitude of a detected displacement or acoustic signal. The term "distortion" means a variation of the signal from a normal signal, e.g., a change in frequency response, etc. The term "peak ratio" means the value of the displacement signal at its maximum value divided by the value of the signal at its minimum value.

Figure 6:
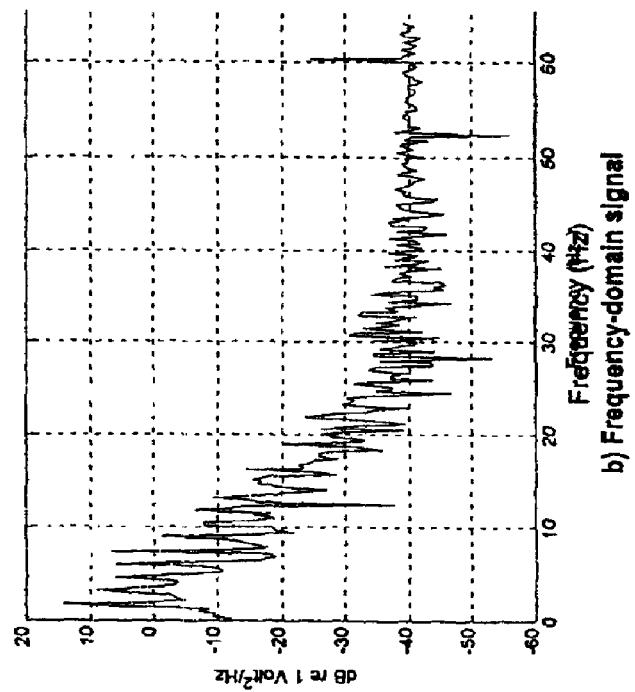
FIGS. 5 and 6 are graphs illustrating time domain and frequency domain responses, respectively, generated by a brain assessment monitor from a healthy patient.
Figure 5:
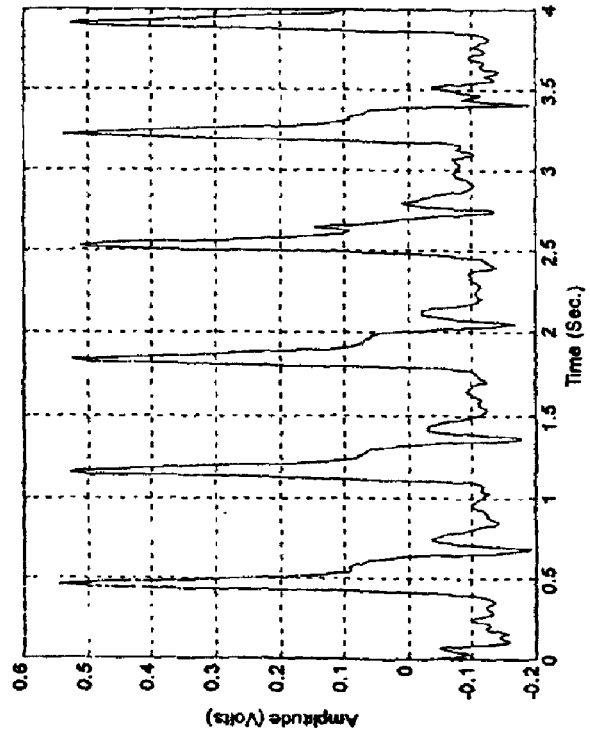

FIGS. 5 and 6 are the time and frequency domain response, respectively, of a healthy patient who had an invasive monitor but who was healthy at the time he was monitored. Note the "clean" character of the signal, the high amplitude, and ratio of the negative to positive values being approximately 3:1 in the time domain. In the frequency response of this patient, his signal exhibits a high fundamental and has harmonics and overtones which diminish to the background noise level by approximately 25 Hz.

Figure 8:
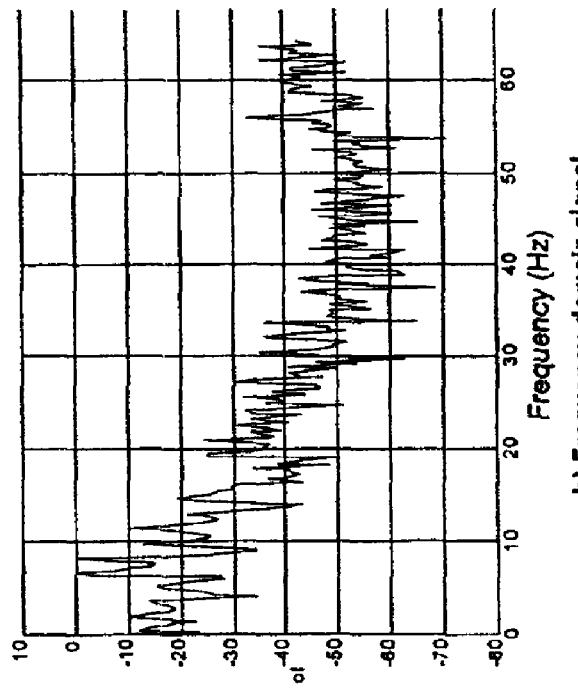
FIGS. 7 and 8 are graphs of time and frequency responses, respectively, generated by a brain assessment monitor from a patient suffering from severe brain damage.
Figure 7:
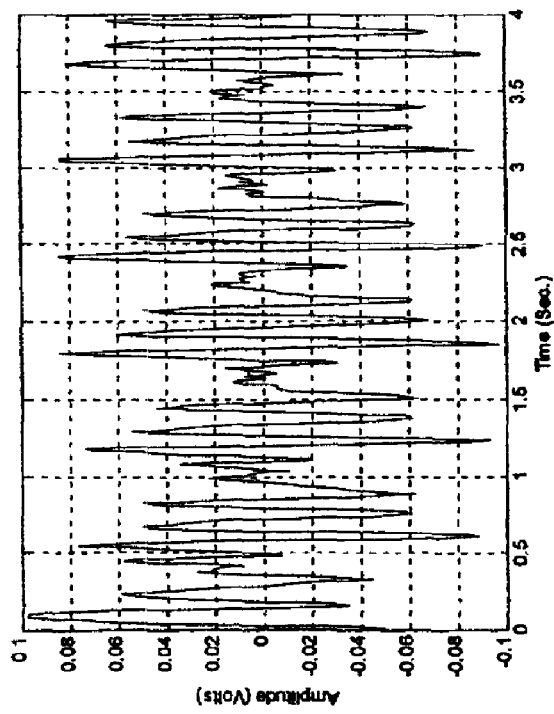

FIGS. 7 and 8 are the time and frequency response, respectively, of a traumatic brain injured patient with a relatively low ICP but who had suffered severe brain damage. By the time of the monitoring session that produced these signal his ICPs were controlled, but his brain was so damaged that he did not survive. Note that the absolute signal amplitude is low compared to the healthy patient and that the frequency domain harmonics actually rise after the fundamental before falling off and then rising again, which is clearly distinct from the healthy patient.

Figure 9:
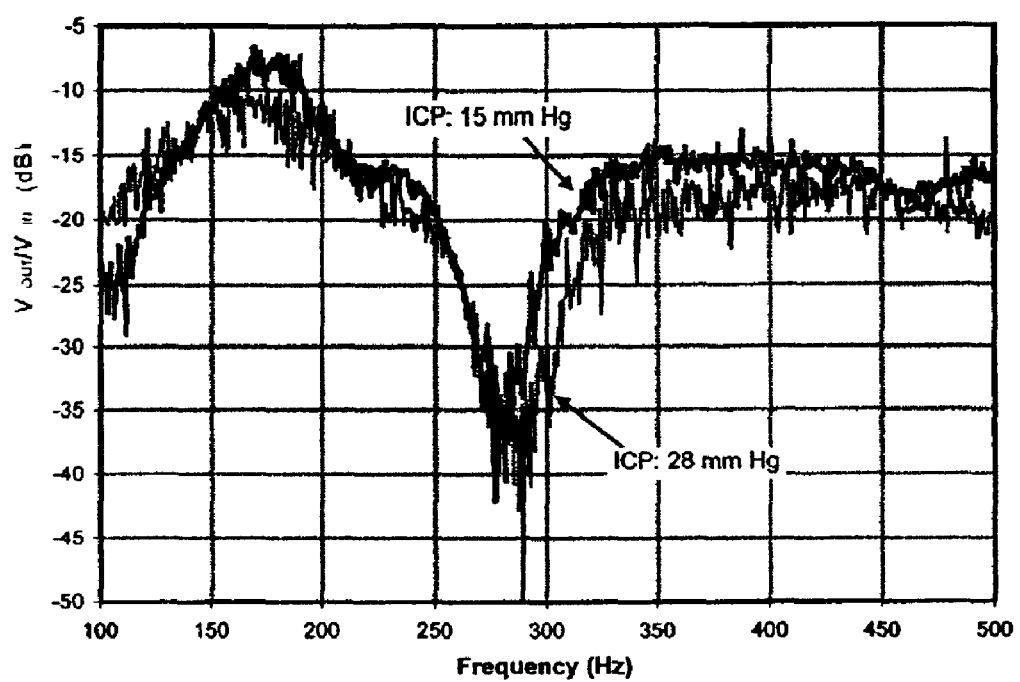
FIG. 9 is a graph including frequency responses of a brain-injured patient at intracranial pressures of 15 and 28 mm Hg.

FIG. 9 shows the frequency response of the brain to a broadband signal of 100 to 500 Hz as a function of increasing ICP. The response is somewhat damped as the ICP increases from 15 to 28 mm Hg and the cerebral perfusion pressure (CPP) drops from 65 to 50, indicating a loss of the autoregulation function. Thus increased ICP accompanied by decreased CPP (i.e., below the critical value of 60 mmHg) contribute to the damped signal response.

Figure 10:
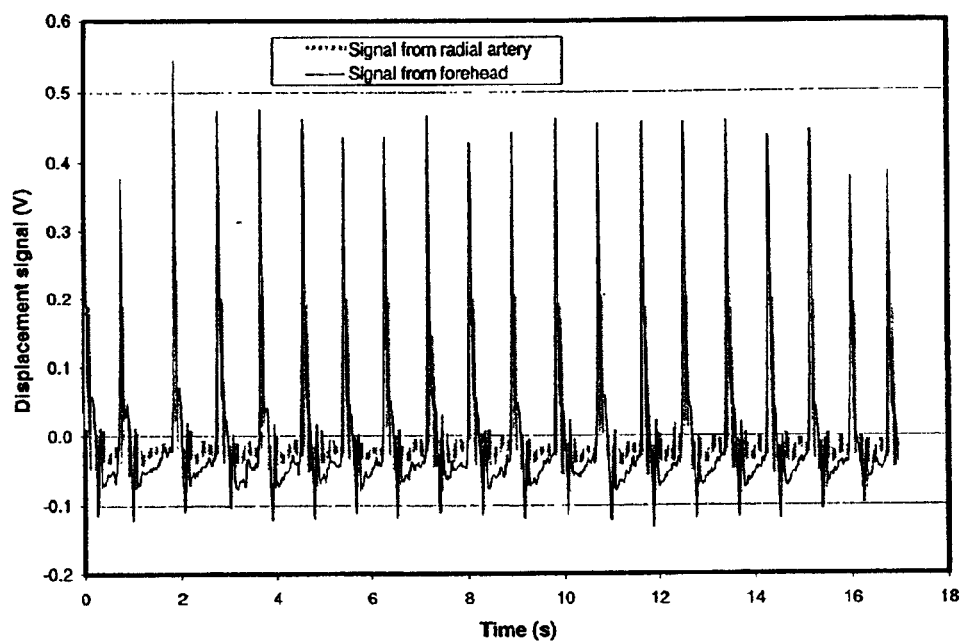
FIG. 10 is a time domain signal.
Figure 11:
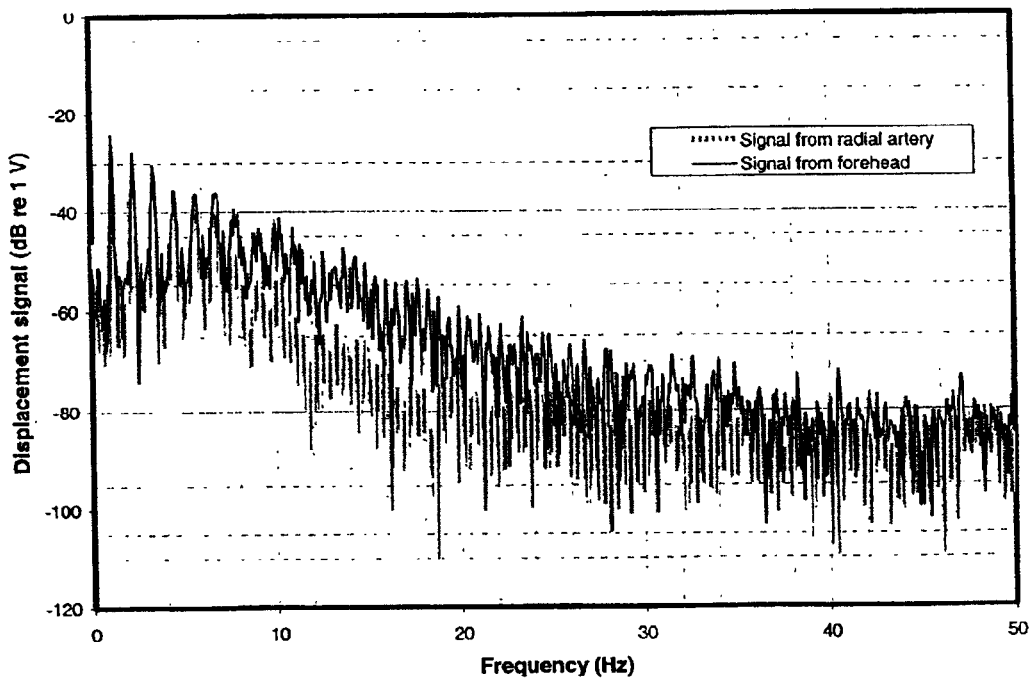
FIG. 11 is a frequency domain signal generated by a brain assessment monitor from a patient suffering from an ischemic stroke.

FIG. 10 shows the time and FIG. 11 the frequency domain signal of a patient with a moderate middle cerebral arterial (MCA) ischemic stroke. In the time domain, note that the signal is negative and somewhat higher in amplitude but otherwise is a good representation of the arterial pulse waveform as would be observed elsewhere in the body. The negative going character and amplitude variation are a function of sensor type and position and not reflective of true signal difference.

In the frequency domain, however, there is a divergence of the signals (the upper trace is from the brain, the lower from another artery in the body), indicating that an excess of energy is present in the higher band, above 10 Hz, compared to the arterial pulse. This plateauing in the frequency domain is much more pronounced in patients with severe trauma, but nevertheless is clearly evident here. This divergence in energy allows for the differentiation of stroke from normal, where there is no divergence. Other signal analyses can be performed to enhance the difference between the two responses such as a discrete Fourier transform (DFT) of the normal signal subtracted from that of the ischemic stroke signal, highlighting the difference of the signal components in the frequency range of interest, e.g., here 10–25 Hz. Normal persons will typically show signal variations of the brain to normal signal of a maximum of 10 dB. Such analysis can quickly show the existence of an anomaly in the signal and when compared to a library of such anomalies can enable identification of the pathology.

Figure 12:
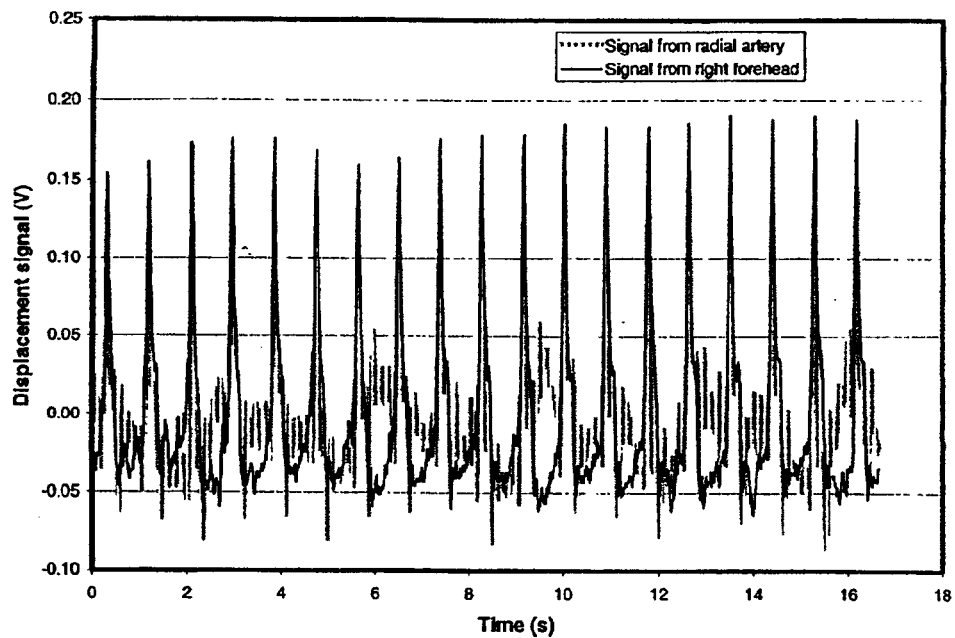
FIG. 12 is a time domain signal and FIG. 13 is a frequency domain signal generated by a brain assessment monitor from a patient suffering from a hemorrhagic stroke.
Figure 13:
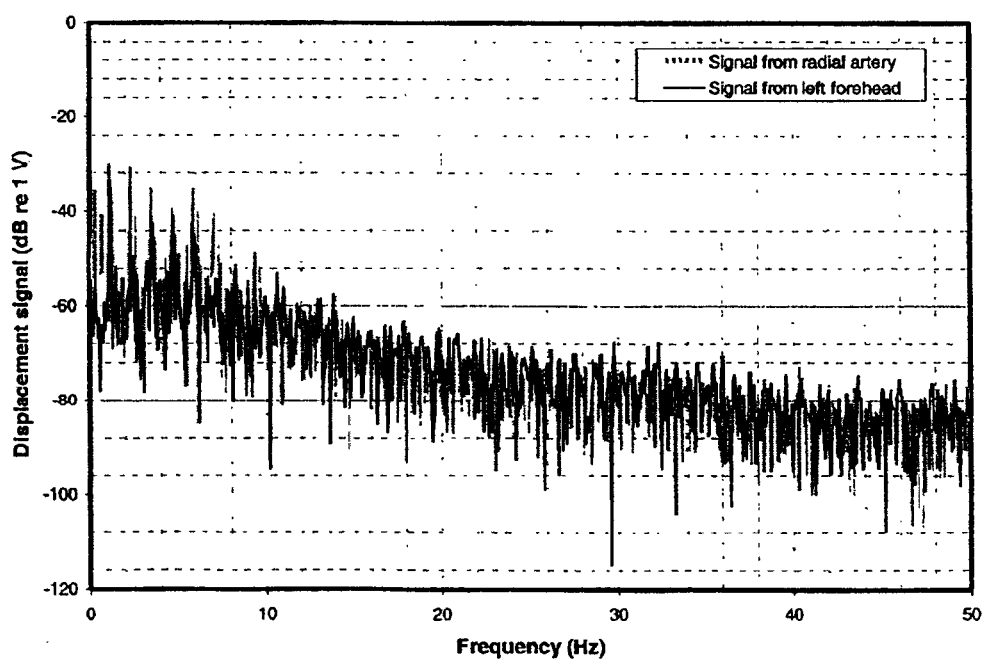

FIG. 12 is the time and FIG. 13 the frequency response of a small subarachnoid hemorrhage of the type that arises in trauma or in many hemorrhagic strokes. The significant element that marks the majority of hemorrhages is the unevenness or roughness of the intra cycle signal character. This can be observed in the "jagged" character of the transition trace between the two pulse points. As can be expected this feature results in a harmonic and overtone content that remains high relative to the fundamental (frequency response portion of the figure) and in so doing differentiates it from events such as small focal contusions or ischemic strokes.

In addition to the above examples, there are alternative embodiments for indicating relative degrees of health of subjects whether healthy, injured or diseased. Signs of these anomalies can be seen from signals measured at individual locations, such as arterial obstruction evidencing itself at a single point, or in comparison with another sensor(s). Other applications of this system may include methods to detect the existence of or propensity toward any type of recognition of altered flow in the vascular system. This can be achieved through monitoring any point where arterial flow secondary to plaques on the arterial walls that can be detected either through the use of a single sensor, or multiple sensors at different points for comparative measurements. Thus, in addition to indicating disease in the brain, the system may be used to indicate compromised brain perfusion as well, which may permit predictions of stroke propensity. The system may also be used to identify potential or existing cardiovascular disease.

Whereas particular embodiments of this invention have been described above for purposes of illustration, it will be evident to those skilled in the art that numerous variations of the details of the present invention may be made without departing from the invention as defined in the appended claims.

What is claimed is:

1. A non-invasive brain assessment monitor comprising:
   a brain sensor configured and adapted to sense acoustic signals generated from pulsing blood flow through a patient's brain, wherein the brain sensor measures frequencies of up to about 20 kHz; and
   means for analyzing the acoustic signals in order to determine whether the patient has undergone a brain injury and/or disease.

2. The brain assessment monitor of claim 1, wherein the brain sensor measures frequencies of from about 0.1 to about 1,000 Hz.

3. The brain assessment monitor of claim 1, wherein the brain sensor measures frequencies of from about 0.5 Hz to about 100 Hz.

4. The brain assessment monitor of claim 1, wherein the brain injury and/or brain disease comprises a stroke.

5. The brain assessment monitor of claim 1, wherein the brain injury and/or brain disease comprises a head trauma.

6. The brain assessment monitor of claim 1, wherein the brain injury and/or brain disease comprises a hemorrhage.

7. The brain assessment monitor of claim 1, wherein the analyzing means includes means for analyzing attenuation of the acoustic signals.

8. The brain assessment monitor of claim 1, wherein the analyzing means includes means for analyzing distortion of the acoustic signals.

9. The brain assessment monitor of claim 1, wherein the analyzing means includes means for comparing positive and negative components of the acoustic signals.

10. The brain assessment monitor of claim 9, wherein a peak ratio of the positive and negative components is determined.

11. The brain assessment monitor of claim 1, further comprising:
    at least one reference sensor configured and adapted to sense acoustic signals generated from another portion of the patient's body; and
    means for comparing the acoustic signals from the brain sensor and reference sensor.

12. The brain assessment monitor of claim 11, wherein the reference sensor comprises an arterial pulse sensor.

13. The brain assessment monitor of claim 12, wherein the arterial pulse sensor is adapted for mounting on a wrist of the patient.

14. The brain assessment monitor of claim 11, wherein the signals from the reference sensor are subtracted from the signals from the brain sensor.

15. The brain assessment monitor of claim 1, further comprising at least one actuator for generating additional acoustic signals in the brain.

16. The brain assessment monitor of claim 1, wherein the monitor is portable.

17. A non-invasive brain assessment monitor comprising:
    a brain sensor configured and adapted for mounting on a patient's head, wherein the brain sensor measures frequencies of up to about 20 kHz;
    a reference sensor configured and adapted for mounting at another location on the patient's body; and means for comparing signals from the brain sensor and the reference sensor to determine whether the patient has undergone a brain injury and/or brain disease.

18. The brain assessment monitor of claim 17, wherein the brain sensor senses acoustic signals generated from pulsing blood flow through the patient's brain.

19. The brain assessment monitor of claim 17, wherein the reference sensor senses an arterial pulse of the patient.

20. The brain assessment monitor of claim 17, wherein the brain sensor senses acoustic signals generated from pulsing blood flow through the patient's brain, and the reference sensor senses an arterial pulse of the patient.

21. The brain assessment monitor of claim 20, wherein the signals from the reference sensor are subtracted from the signals from the brain sensor.

22. The brain assessment monitor of claim 17, wherein the brain sensor measures frequencies of from about 0.1 to about 1,000 Hz.

23. The brain assessment monitor of claim 17, wherein the brain sensor measures frequencies of from about 0.5 to about 100 Hz.

24. The brain assessment monitor of claim 17, wherein the brain injury and/or brain disease comprises a stroke.

25. The brain assessment monitor of claim 17, wherein the brain injury and/or brain disease comprises a head trauma.

26. The brain assessment monitor of claim 17, wherein the brain injury and/or brain disease comprises a hemorrhage.

27. The brain assessment monitor of claim 17, wherein the comparing means includes means for analyzing attenuation of signals from the brain sensor.

28. The brain assessment monitor of claim 17, wherein the comparing means includes means for analyzing distortion of signals from the brain sensor.

29. The brain assessment monitor of claim 17, wherein the comparing means comprises means for comparing positive and negative components of signals from the brain sensor.

30. The brain assessment monitor of claim 29, wherein a peak ratio of the positive and negative components is determined.

31. The brain assessment monitor of claim 17, further comprising at least one actuator for generating acoustic signals in the brain.

32. The brain assessment monitor of claim 17, wherein the monitor is portable.

33. A method of monitoring brain injury and/or brain disease of a patient, the method comprising:
  mounting a non-invasive brain sensor capable of measuring frequencies of up to about 20 kHz on the head of the patient to sense acoustic signals generated from pulsing blood flow characteristics through a patient's brain;
  sensing acoustic signals with the brain sensor generated from pulsing blood flow through the patient's brain; and
  analyzing the acoustic signals to determine whether the patient has undergone a brain injury and/or brain disease.

34. A method of monitoring brain injury and/or brain disease of a patient, the method comprising:
  mounting a non-invasive brain sensor to sense acoustic signals generated from pulsing blood flow characteristics capable of measuring frequencies of up to about 20 kHz on the patient's head to sense acoustic signals generated from pulsing blood flow characteristics through a patient's brain;
  mounting a reference sensor at another location on the patient's body; and
  comparing signals from the brain sensor and the reference sensor to determine whether the patient has undergone a brain injury and/or brain disease.

35. A non-invasive brain assessment monitor comprising:
  a brain sensor configured and adapted to sense acoustic signals generated from pulsing blood flow through a patient's brain; and
  means for analyzing the acoustic signals in order to determine whether the patient has undergone a brain injury and/or brain disease without the application of an external signal, wherein the analyzing means includes means for analyzing attenuation of the acoustic signals.

36. A non-invasive brain assessment monitor comprising:
  a brain sensor configured and adapted to sense acoustic signals generated from pulsing blood flow through a patient's brain; and
  means for analyzing the acoustic signals in order to determine whether the patient has undergone a brain injury and/or brain disease without the application of an external signal, wherein the analyzing means includes means for analyzing distortion of the acoustic signals.

37. A non-invasive brain assessment monitor comprising:
  a brain sensor configured and adapted to sense acoustic signals generated from pulsing blood flow through a patient's brain; and
  means for analyzing the acoustic signals in order to determine whether the patient has undergone a brain injury and/or brain disease without the application of an external signal, wherein the analyzing means includes means for comparing positive and negative components of the acoustic signals.

38. A non-invasive brain assessment monitor comprising:
  a brain sensor configured and adapted to sense acoustic signals generated from pulsing blood flow through a patient's brain;
  means for analyzing the acoustic signals in order to determine whether the patient has undergone a brain injury and/or brain disease;
  at least one reference sensor, adapted for mounting on a wrist of a patient and comprising an arterial pulse sensor, for sensing acoustic signals generated from another portion of the patient's body; and
  means for comparing the acoustic signals from the brain sensor and reference sensor without the application of an external signal.

39. A non-invasive brain assessment monitor comprising:
  a brain sensor configured and adapted to sense acoustic signals generated from pulsing blood flow through a patient's brain;
  means for analyzing the acoustic signals in order to determine whether the patient has undergone a brain injury and/or brain disease without the application of an external signal; and
  at least one actuator for generating additional acoustic signals in the brain.

40. A non-invasive brain assessment monitor comprising:
  a brain sensor configured and adapted to sense acoustic signals generated from pulsing blood flow through a patient's brain for mounting on a patient's head;
  a reference sensor configured and adapted for mounting at another location on the patient's body; and
  means for comparing signals from the brain sensor and the reference sensor to determine whether the patient has undergone a brain injury and/or brain disease without the application of an external signal, wherein the comparing means includes means for analyzing attenuation of signals from the brain sensor.

41. A non-invasive brain assessment monitor comprising:

a brain sensor configured and adapted to sense acoustic signals generated from pulsing blood flow through a patient's brain for mounting on a patient's head;

a reference sensor configured and adapted for mounting at another location on the patient's body; and means for comparing signals from the brain sensor and the reference sensor to determine whether the patient has undergone a brain injury and/or brain disease without the application of an external signal, wherein the comparing means includes means for analyzing distortion of signals from the brain sensor.

42. A non-invasive brain assessment monitor comprising:

a brain sensor configured and adapted to sense acoustic signals generated from pulsing blood flow through a patient's brain for mounting on a patient's head;

a reference sensor configured and adapted for mounting at another location on the patient's body; and means for comparing signals from the brain sensor and the reference sensor to determine whether the patient has undergone a brain injury and/or brain disease without the application of an external signal, wherein the comparing means comprises means for comparing positive and negative components of signals from the brain sensor.

43. A non-invasive brain assessment monitor comprising:

a brain sensor configured and adapted to sense acoustic signals generated from pulsing blood flow through a patient's brain for mounting on a patient's head;

a reference sensor configured and adapted for mounting at another location on the patient's body; and means for comparing signals from the brain sensor and the reference sensor to determine whether the patient has undergone a brain injury and/or brain disease without the application of an external signal; and at least one actuator for generating acoustic signals in the brain.

* * * * *